US012779124B2

(12) United States Patent
Kim et al.

(10) Patent No.: US 12,779,124 B2
(45) Date of Patent: Nov. 3, 2026

(54) SYRINGE-TYPE MICRONEEDLE

(71) Applicant: THERAJECT ASIA Co., Ltd., Daejeon (KR)

(72) Inventors: Kyung Dong Kim, Daejeon (KR); A Reum Han, Asan-si (KR)

(73) Assignee: THERAJECT ASIA CO., LTD., Daejeon (KR)

( * ) Notice: Subject to any disclaimer, the term of this patent is extended or adjusted under 35 U.S.C. 154(b) by 534 days.

(21) Appl. No.: 18/554,467

(22) PCT Filed: Mar. 25, 2022

(86) PCT No.: PCT/KR2022/004266
§ 371 (c)(1),
(2) Date: Oct. 7, 2023

(87) PCT Pub. No.: WO2022/225208
PCT Pub. Date: Oct. 27, 2022

(65) Prior Publication Data

US 2024/0033433 A1 Feb. 1, 2024

(30) Foreign Application Priority Data

Apr. 20, 2021 (KR) ........................ 10-2021-0050926

(51) Int. Cl.
*A61M 5/20* (2006.01)
*A61M 5/32* (2006.01)
*A61M 5/31* (2006.01)

(52) U.S. Cl.
CPC .......... *A61M 5/2053* (2013.01); *A61M 5/329* (2013.01); *A61M 2005/3123* (2013.01)

(58) Field of Classification Search
CPC .. A61M 5/2053; A61M 5/329; A61M 5/3295; A61M 5/3298; A61M 7/0015; A61M 2307/0023; A61K 9/0021
See application file for complete search history.

(56) References Cited

U.S. PATENT DOCUMENTS 2,551,902 A * 5/1951 Rieck .................. A61M 5/3202 604/173
4,323,066 A * 4/1982 Bourdon ............. A61M 5/2053 604/228
(Continued)

FOREIGN PATENT DOCUMENTS

JP 2018-191702 A 12/2018
KR 10-2010-0101329 A 9/2010
(Continued)

*Primary Examiner* — Gerald L Sung
(74) *Attorney, Agent, or Firm* — You & IP, LLC

(57) ABSTRACT

According to the present disclosure, by a simple operation of pressing the press-fitting block with the pressing part, a press-fitting force of the press-fitting block is automatically released at a predetermined time after the needle part penetrates a skin layer, due to the release of the press-fitting force of the press-fitting block, a practitioner can easily determine a time to detach and separate the needle part, due to guiding of the time to detach and separate the needle part, even an unskilled person can easily use the microneedle, by a uniform amount of drug being injected into patients, the same therapeutic effect can be given to the patients, and in particular, by the needle part being promptly removed after the drug of the needle part is injected into the skin layer, there is no concern about the needle part staying in the skin layer for an excessive amount of time.

5 Claims, 5 Drawing Sheets

(56) References Cited

U.S. PATENT DOCUMENTS

| | | | | |
|---|---|---|---|---|
| 10,342,964 | B2 | 7/2019 | Takada et al. | |
| 2003/0216695 | A1* | 11/2003 | Yang | A61M 5/2053 604/141 |
| 2008/0097379 | A1* | 4/2008 | Dacquay | A61F 9/0008 604/113 |
| 2009/0163868 | A1* | 6/2009 | Hoel | A61M 37/0015 604/141 |
| 2020/0093996 | A1* | 3/2020 | An | A61N 1/06 |
| 2022/0379044 | A1* | 12/2022 | Chitnis | A61F 9/0017 |

FOREIGN PATENT DOCUMENTS

| | | | |
|---|---|---|---|
| KR | 10-2011-0113797 | A | 10/2011 |
| KR | 10-2015-0122367 | A | 11/2015 |
| KR | 10-2016-0125420 | A | 10/2016 |
| KR | 10-2309710 | B1 | 10/2021 |

* cited by examiner

SYRINGE-TYPE MICRONEEDLE

FIELD OF THE INVENTION

The present disclosure relates to a microneedle, and more particularly, to a syringe-type microneedle in which a press-fitting block is pushed by a sealing pressure in an air residence space of a housing and causes a needle part to penetrate the skin, and when an air discharge hole is opened due to the movement of the press-fitting block, as air in the air residence space is discharged through the air discharge hole, press-fitting of the press-fitting block is released.

DISCUSSION OF RELATED ART

Generally, in recent years, technologies relating to various microstructures including a microneedle have been proposed to address pain at an injection site, local damage to the skin, bleeding, and disease transmission at an injection site which are problems of a method of injecting a drug using an injection needle.

The microstructure is a structure for efficient delivery of a drug delivered through the skin and is a patch-type painless syringe for injecting a drug without pain using a microneedle.

The microstructure needs to be used for a certain amount of time (for example, 30 minutes to 8 hours or more) while in contact with the human skin surface (especially, facial skin), and in recent years, a microneedle patch which is a type of patch adhered to the skin has been commonly used to safely attach the microstructure to the skin and maintain the microstructure.

Patent Document 1 (KR 10-2015-0122367 A) discloses a conventional depth adjustment-type injection needle using a microneedle. Referring to Patent Document 1, the depth adjustment-type injection needle includes an injection needle hub formed in a cylindrical shape and having a plurality of microneedles formed on a front surface thereof, a rotating body formed in a hollow shape with open front and rear portions and having internal screw threads formed on an inner circumferential surface thereof to allow insertion of the injection needle hub, an injection needle cap formed in a hollow shape with an open rear end and having external screw threads formed on an outer circumferential surface thereof to be coupled to the internal screw threads and a through-hole formed on a front surface thereof to correspond to the microneedle, and a protective cap configured to surround and cover the front surface of the injection needle cap and block supply of contaminated air into the through-hole.

Here, the injection needle hub includes a front end portion configured to fix the microneedle and have a connection passage formed therein to guide a drug to move to the microneedle and a rear end portion formed to extend from a rear end of the front end portion and have an insertion groove formed thereinto to communicate with the connection passage and allow a syringe cylinder to be coupled.

Here, when the injection needle cap is rotated in a predetermined direction to cause the external screw threads to rotate along the internal screw threads of the rotating body, the rotating body rotates to be lifted or lowered based on the injection needle cap, the height of the rotating body is adjusted, and in that state, when the injection needle hub is pressed to move toward the injection needle cap through the rotating body, the microneedle is exposed through the through-hole and penetrates the skin.

That is, as the height of the rotating body is adjusted based on the injection needle cap, the length at which the microneedle is exposed through the through-hole of the injection needle cap is adjusted, and the length of the microneedle penetrating the skin is changed.

However, in Patent Document 1 (KR 10-2015-0122367 A) described above, a practitioner should directly determine the time during which the microneedle exposed through the injection needle cap stays in the skin after penetrating the skin, and variations occur in the time during which a drug is injected into the skin layer while the microneedle stays in the skin according to medical skill of the practitioner, which makes it difficult to inject a uniform amount of the drug into patients. Also, in the case of an unskilled practitioner, it is difficult to determine the time during which the drug of the microneedle is injected into the skin, and there is an inconvenience of having to let the microneedle stay in the skin for a long period of time, and here, skin damage or necrosis of skin tissue may occur due to the microneedle staying in the skin for an excessive amount of time, and in the process of press-fitting the injection needle hub, as the front surface of the injection needle cap that is in close contact with the skin slides on the skin layer, the microneedle penetrating the skin may move in the skin layer, and there is a concern that a patient may feel pain due to the movement of the microneedle in the skin layer, and accordingly, there is a problem that product reliability is degraded.

SUMMARY OF THE INVENTION

The present disclosure is directed to providing a syringe-type microneedle including a housing in which an air discharge hole communicating with an internal air residence space is formed in an outer circumferential surface, a press-fitting block configured to open and close the air discharge hole formed in the housing, a needle part formed on a bottom surface of the press-fitting block, a pressing part formed in the air residence space of the housing, and a protective film configured to seal a lower end of the housing, wherein, when the protective film is removed and the pressing part is pressed to cause the press-fitting block to move downward by an air pressure in the air residence space, the needle part formed on the press-fitting block is exposed to a bottom of the housing and penetrates a patient's skin to inject a drug, and as air in the air residence space is discharged to the outside while the air discharge hole is opened by the press-fitting block, press-fitting of the press-fitting block is released, and a time to detach the needle part penetrating the skin is guided.

The present disclosure provides a syringe-type microneedle including: a housing formed in a hollow shape with open upper and lower portions and having an air discharge hole formed in an outer circumferential surface thereof and an air residence space formed therein to communicate with the air discharge hole; a press-fitting block inserted into the air residence space of the housing and configured to come in close contact with an inner circumferential surface of the air residence space of the housing to seal the air discharge hole and open and close the air discharge hole to allow air in the air residence space to be discharged to the outside through the air discharge hole; a needle part installed on a bottom surface of the press-fitting block, formed to contain a drug made of a predetermined substance, and configured to be exposed to a bottom of the housing and penetrate the skin due to the press-fitting block; a pressing part inserted into and coupled to the air residence space to be positioned above the press-fitting block and configured to push the air in the air residence space toward the press-fitting block to guide downward movement of the press-fitting block; and a protective film formed to be attached to seal a lower end of the housing and prevent contaminants contained in air from entering the needle part.

In the syringe-type microneedle according to the present disclosure, a stopper formed along the inner circumferential surface of the air residence space to prevent a lower end of the pressing part from coming in contact with the press-fitting block may be further formed in the housing.

In the syringe-type microneedle according to the present disclosure, catching steps formed to be bent in directions facing each other on an edge of the lower end of the housing and configured to allow an edge of the bottom surface of the press-fitting block to be caught to block movement of the press-fitting block toward the lower end of the housing by a predetermined distance or more; and an adhesive film formed on bottom surfaces of the catching steps and configured to be adhered to the skin and prevent movement of the housing may be further formed in the housing.

In the syringe-type microneedle according to the present disclosure, in the housing, a distance from the air discharge hole to the lower end of the housing may be formed to be relatively larger than a height of the press-fitting block.

In the syringe-type microneedle according to the present disclosure, the needle part may be formed to have any one structure of a coating type structure having a drug coated on an outer surface thereof, a melting type structure configured to melt after penetrating the skin, and a drug injection type structure having a drug accommodated therein and configured to penetrate the skin to inject the drug.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, embodiments of the present disclosure will be described in more detail with reference to the accompanying drawings.

Figure 1:
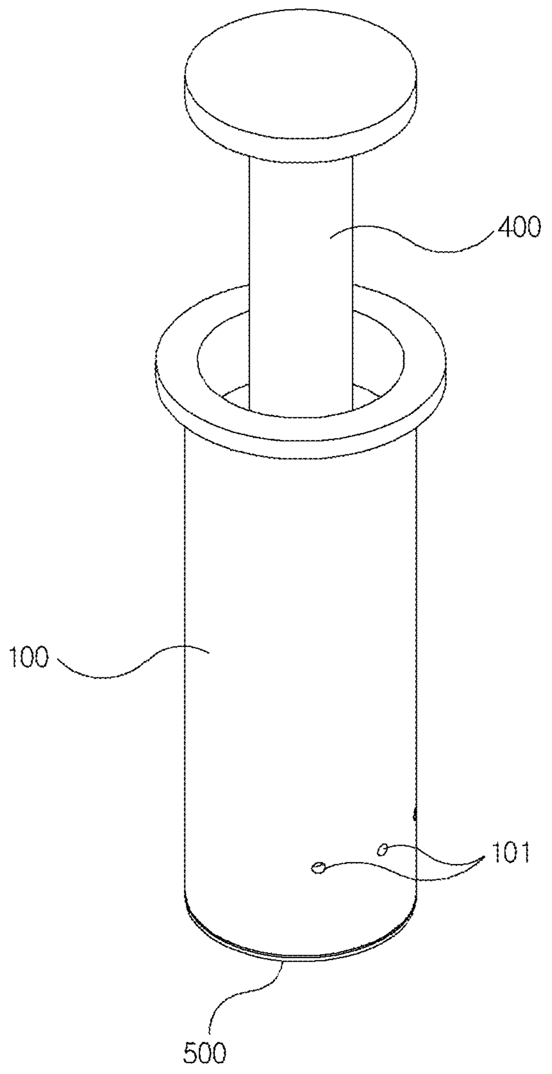
FIG. 1 is a perspective view illustrating a syringe-type microneedle according to the present disclosure.
Figure 2:
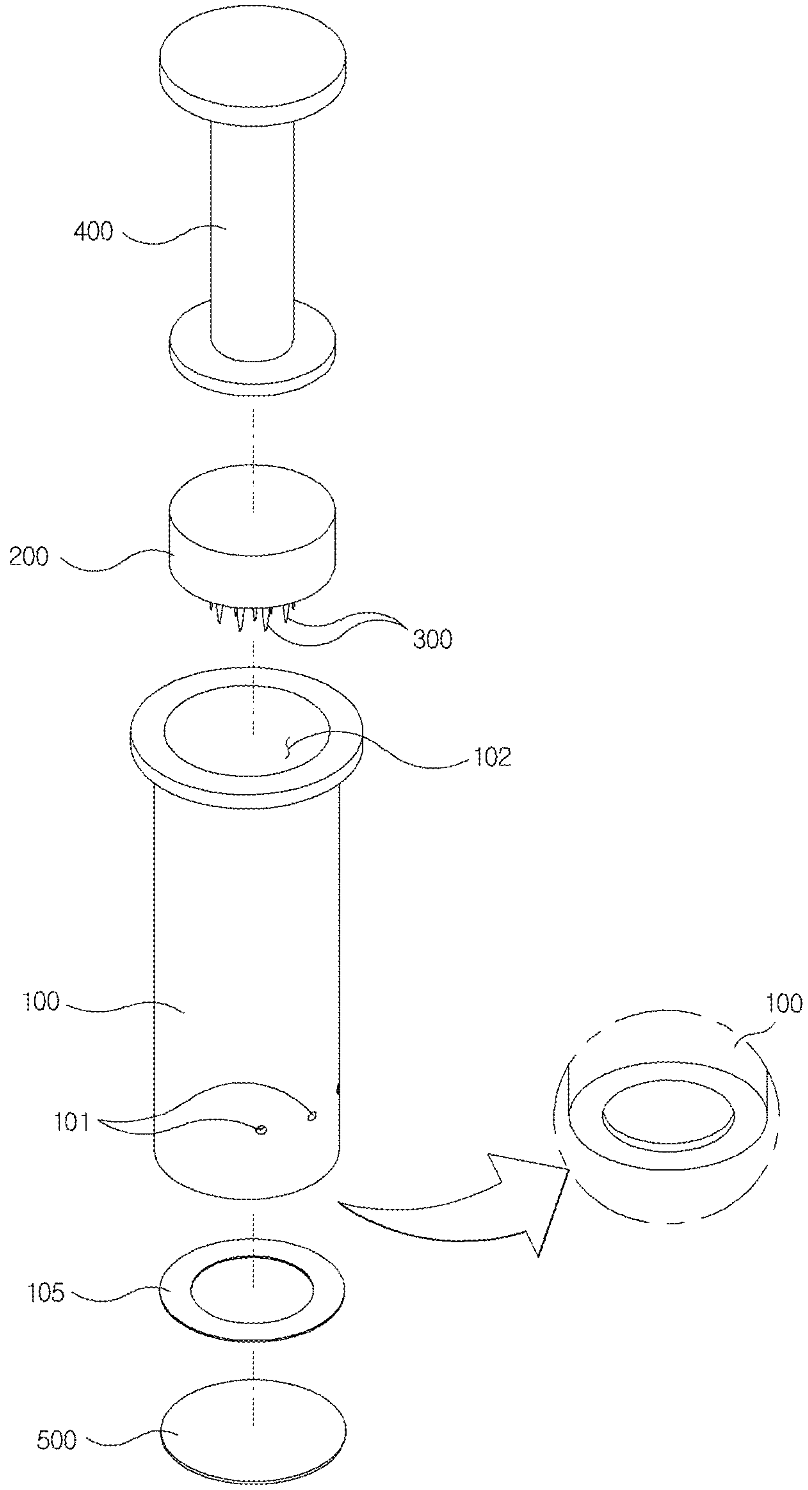
FIG. 2 is an exploded perspective view of FIG. 1.
Figure 3:
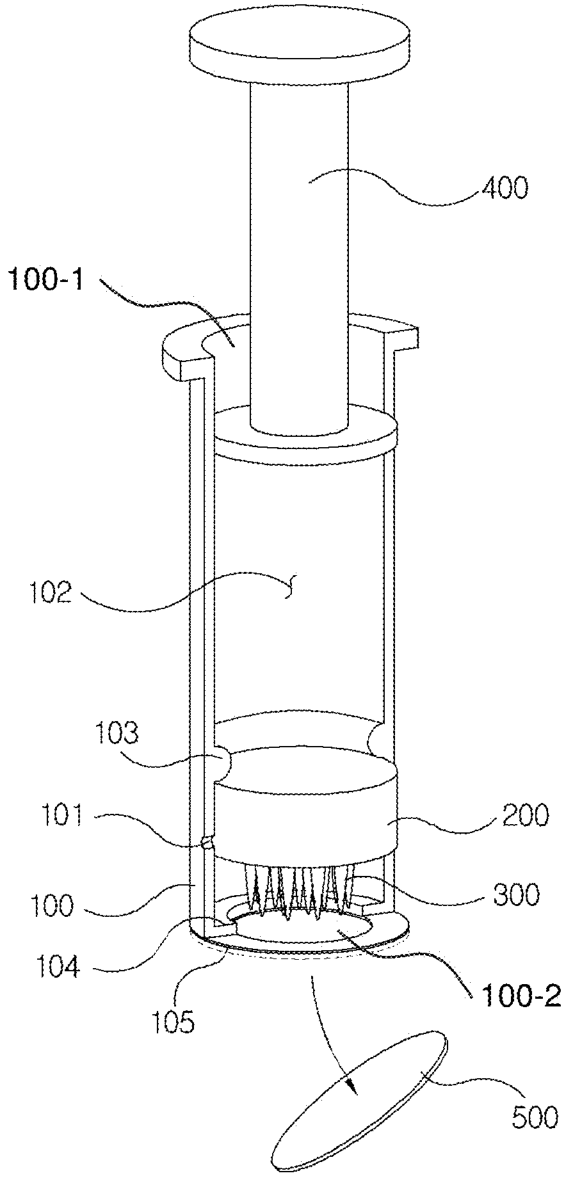
FIG. 3 is a cross-sectional perspective view illustrating a state in which a protective film is separated from the syringe-type microneedle according to the present disclosure.
Figure 4:
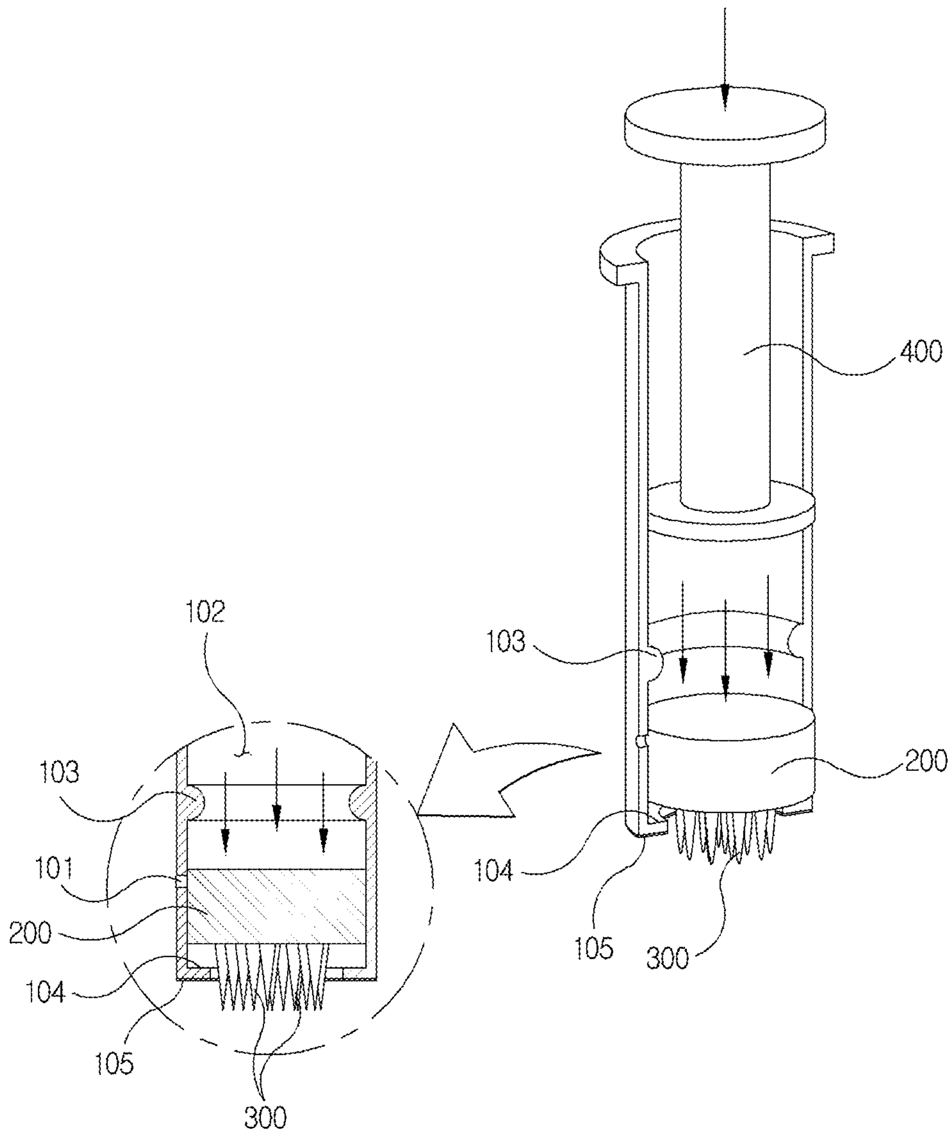
FIG. 4 is a cross-sectional perspective view illustrating a state in which a moving block is pressed downward by a pressing part of the syringe-type microneedle according to the present disclosure.
Figure 5:
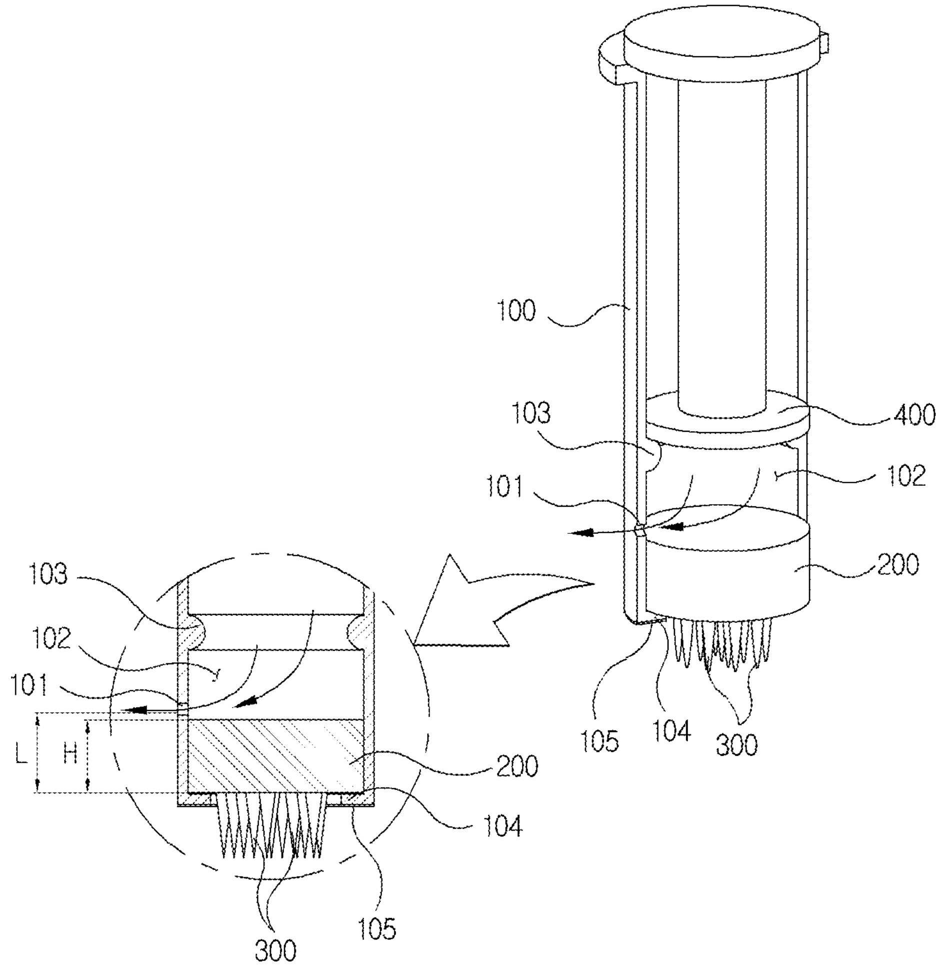
FIG. 5 is a cross-sectional perspective view illustrating a state in which air is discharged through an air discharge hole of the syringe-type microneedle according to the present disclosure.

Referring to FIGS. 1 to 5, a housing 100 has a hollow space formed therein and openings 100-1 and 100-2 respectively formed at top and bottom ends and has an air discharge hole 101 formed in an outer circumferential surface thereof and an air residence space 102 formed therein to communicate with the air discharge hole 101.

A lower end of the housing 100 comes in close contact with a skin surface that corresponds to a skin layer to be penetrated by a needle part 300.

The housing 100 may be formed in a cylindrical shape and accommodate a press-fitting block 200 and a pressing part 400 therein.

The housing 100 accommodates air in the air residence space 102.

A stopper 103 formed along an inner circumferential surface of the air residence space 102 to prevent a lower end of the pressing part 400 from coming in contact with the press-fitting block 200 is further formed in the housing 100.

The stopper 103 prevents the lower end of the pressing part 400 from approaching the press-fitting block 200 and corning in close contact with an upper end of the press-fitting block 200 or the press-finking block 200 from moving upward and coming in close contact with the lower end of the pressing part 400.

The stopper 103 restricts movement of the lower end of the pressing part 400 to block the pressing part 400 from entering the air residence space 102 at a predetermined depth or more.

The stopper 103 may be formed at a position that is relatively higher than a height of the air discharge hole 101.

The air discharge hole 101 is formed as one or more air discharge holes 101, and upon being opened by the press-fitting block 200, the air discharge holes 101 communicate with the air residence space 102 and allow air in the air residence space 102 to be discharged to the outside.

The air discharge holes 101 may be formed on the same horizontal line.

In the housing 100, a distance L from the air discharge hole 101 to the lower end of the housing 100 is formed to be relatively larger than a height H of the press-fitting block 200.

The air discharge hole 101 may be formed at a position that is relatively higher than the press-fitting block 200 moved to the lower end of the housing 100.

Catching steps 104 formed to be bent in directions facing each other on an edge of the lower end of the housing 100 and configured to allow an edge of a bottom surface of the press-fitting block 200 to be caught to block movement of the press-fitting block 200 toward the lower end of the housing 100 by a predetermined distance or more and an adhesive film 105 formed on bottom surfaces of the catching steps 104 and configured to be adhered to the skin and prevent movement of the housing 100 are further formed in the housing 100.

The catching steps 104 are formed so that interference with the needle part 300 exposed to the bottom of the housing 100 is prevented. The catching steps 104 restrict movement of the press-fitting block 200.

The adhesive film 105 is formed in a double-sided tape structure and has an upper surface attached to the catching step 104 and a bottom surface attached to the skin surface to prevent the housing 100 from sliding on the skin surface.

The adhesive film 105 is attached to the skin surface, and when the needle part 300 penetrates the skin, blocks contaminants contained in air from entering the housing 100 through a gap between the lower end of the housing 100 and the skin surface.

The press-fitting block 200 is inserted into the air residence space 102 of the housing 100 and comes in close contact with the inner circumferential surface of the air residence space 102 of the housing 100 to seal the air discharge hole 101 and opens and closes the air discharge hole 101 to allow air in the air residence space 102 to be discharged to the outside through the air discharge hole 101.

The press-fitting block 200 is formed of a rubber or silicone material having an elastic force and comes in close contact with the inner circumferential surface of the air residence space 102.

The press-fitting block 200 moves downward due to being pushed by air pressure in the air residence space 102.

The press-fitting block 200 reaches the lower end of the housing 100 and opens the air discharge hole 101 of the housing 100.

The press-fitting block 200 is blocked by the stopper 103 of the housing 100 and prevented from moving upward in the air residence space 102.

The press-fitting block 200 may be formed to have a diameter equal to a diameter of the lower end of the pressing part 400.

The press-fitting block 200 is installed in the air residence space 102 and causes the needle part 300 to be positioned in the housing 100.

The height H of the press-fitting block 200 is firmed to be relatively smaller than the distance L from the lower end of the housing 100 to the air discharge hole 101.

The needle part 300 is installed on the bottom surface of the press-fitting block 200, is formed to contain a drug made of a predetermined substance, and is exposed to a bottom of the housing 100 and penetrates the skin due to the press-fitting block 200.

The needle part 300 is formed as a plurality of needle parts 300 spaced apart at predetermined intervals on the bottom surface of the press-fitting block 200.

The needle parts 300 inject a drug into the skin layer while penetrating the skin due to being pressed by the press-fitting block 200.

The needle parts 300 are formed to have any one structure of a coating type structure having a drug coated on an outer surface thereof, a melting type structure configured to melt after penetrating the skin, and a drug injection type structure having a drug accommodated therein and configured to penetrate the skin to inject the drug.

The pressing part 400 is inserted into and coupled to the air residence space 102 to be positioned above the press-fitting block 200 and pushes the air in the air residence space 102 toward the press-fitting block 200 to guide downward movement of the press-fitting block 200.

The lower end of the pressing part 400 is formed of a rubber or silicone material having an elastic force and comes in close contact with the inner circumferential surface of the air residence space 102.

The pressing part 400 compresses the air in the air residence space 102 downward while moving downward and forces the press-fitting block 200 to be pushed and moved downward due to the compressed air.

The pressing part 400 has an upper end caught at an upper end of the housing 100 and is prevented from entering the housing 100 by a predetermined distance or more.

The pressing part 400 has a lower end blocked by the stopper 103 of the housing 100 and is prevented from coming in close contact with an upper surface of the press-fitting block 200.

A protective film 500 is formed to be attached to seal the lower end of the housing 100 and prevents contaminants contained in air from entering the needle part 300.

The protective film 500 may be attached to the adhesive film 105 to seal the lower end of the housing 100.

The syringe-type microneedle according to the present disclosure configured as described above is used as follows.

First, the syringe-type microneedle at which the needle part 300 containing a substance to be injected into a patient is installed is provided, and the protective film 500 attached to the lower end of the housing 100 of the syringe-type microneedle is detached and separated therefrom.

Here, as the protective film 500 is detached and separated from the lower end of the housing 100, the adhesive film 105 attached to the bottom surfaces of the catching steps 104 is exposed, and the adhesive film 105 is attached to a skin surface, which corresponds to the skin layer into which a drug will be injected, to attach and fix the lower end of the housing 100 to the skin surface.

Next, the pressing part 400 exposed to a top of the housing 100 is pressed to press air accommodated in the air residence space 102 between the lower end of the pressing part 400 and the press-fitting block 200 downward.

Then, as the pressing part 400 slides downward in the air residence space 102 of the housing 100, the air in the air residence space 102 is compressed, and in that state, as the pressing part 400 continuously moves downward, the compressed air is pushed downward.

Here, the air in the air residence space 102 is compressed by the pressing part 400, and at the time the pressure of the compressed air is increased to a predetermined pressure or more, the press-fitting block 200 is pushed by the compressed air and moves downward.

Here, the press-fitting block 200 is fixed in the air residence space 102 while closing the air discharge hole 101 of the housing 100 and then moves downward due to being pushed by the compressed air moving downward due to the pressing part 400.

Here, the lower end of the pressing part 400 is blocked by the stopper 103 of the housing 100, and the pressing part 400 is prevented from entering the air residence space 102 of the housing 100 at a predetermined depth or more and prevented from coming in close contact with the press-fitting block 200.

Then, the needle part 300 installed on the press-fitting block 200 is exposed to a bottom of the housing 100 and gradually penetrates the skin layer to inject the drug into the skin layer.

Here, an edge of the bottom surface of the press-fitting block 200 is caught at the catching steps 104 of the housing 100, and the press-fitting block 200 is prevented from being detached to the bottom of the housing 100.

Here, the needle part 300 injects the drug into the skin layer by being formed to have any one structure of a coating type structure having a drug coated on an outer surface thereof, a melting type structure configured to melt after penetrating the skin, and a drug injection type structure having a drug accommodated therein and configured to penetrate the skin to inject the drug.

Next, when the press-fitting block 200 moves to the lower end of the housing 100 due to being pushed by the compressed air in the air residence space 102, the air discharge hole 101 is opened and communicates with the air residence space 102, and here, the air in the air residence space 102 is discharged to the outside of the housing 100 through the air discharge hole 101.

Then, as the air in the air residence space 102 is discharged to the outside, the compressed air pressing the press-fitting block 200 in the air residence space 102 gradually disappears, and accordingly, a pressing force of the press-fitting block 200 is released.

Simultaneously, due to the discharge of the air from inside the air residence space 102, a press-fitting force of the pressing part 400 is released, and here, a practitioner detects the time the press-fitting force of the pressing part 400 is released and detaches the housing 100 upward to detach the needle part 300 from the skin layer.

Also, when the housing 100 is detached upward, the adhesive film 105 is simultaneously detached from the skin surface to prevent the adhesive film 105 from remaining on the skin surface.

Here, the time the press-fitting force of the pressing part 400 is released corresponds to a time at which the needle part 300 has completed injection of the drug into the skin layer.

Also, the syringe-type microneedle used as described above is a disposable product and is discarded after use.

According to the above-described structure in z which the air in the air residence space 102 is compressed and pushed with the pressing part 400 to allow the needle part 300 formed on the press-fitting block 200 to penetrate the skin, and at the time the press-fitting block 200 reaches the lower end of the housing due to the compressed air, the air in the air residence space 102 is discharged to the outside through the air discharge hole 101, and pressing of the press-fitting block 200 is released, by a simple operation of pressing the press-fitting block 200 with the pressing part 400, a press-fitting force of the press-fitting block 200 is automatically released at a predetermined time after the needle part 300 penetrates the skin layer, due to the release of the press-fitting force of the press-fitting block 200, a practitioner can easily determine a time to detach and separate the needle part 300, due to guiding of the time to detach and separate the needle part 300, even an unskilled person can easily use the microneedle, and by a uniform amount of drug being injected into patients, the same therapeutic effect can be given to the patients.

According to the present disclosure, by a simple operation of pressing a press-fitting block with a pressing part, a press-fitting force of the press-fitting block is automatically released at a predetermined time after a needle part penetrates a skin layer, due to the release of the press-fitting force of the press-fitting block, a practitioner can easily determine a time to detach and separate the needle part, due to guiding of the time to detach and separate the needle part, even an unskilled person can easily use the microneedle, by a uniform amount of drug being injected into patients, the same therapeutic effect can be given to the patients, and in particular, by the needle part being promptly removed after the drug of the needle part is injected into the skin layer, there is no concern about the needle part staying in the skin layer for an excessive amount of time. Thus, an occurrence of skin damage or necrosis of skin tissue due to the needle part staying in the skin layer is prevented, and since the needle part penetrates the skin while a lower end of a housing is in contact with the skin, there is no concern about movement of the housing on the skin surface. Accordingly, there is an advantage that product reliability is improved.

The syringe-type microneedle according to the present disclosure that has been described above is not limited to the above embodiments, and those of ordinary skill in the art to which the present disclosure pertains may make various changes without departing from the gist of the present disclosure claimed in the claims below Such changes also belong to the technical spirit of the present disclosure.

What is claimed is:

1. A syringe type-microneedle comprising:

a housing (100) having a hollow space formed therein and openings respectively formed at top and bottom ends thereof, and having an air discharge hole (101) formed in an outer circumferential surface thereof and an air residence space (102) formed by the hollow space to communicate with the air discharge hole (101);

a press-fitting block (200) inserted into the air residence space (102) of the housing (100), and configured to come in contact with an inner circumferential surface of the housing (100) and to open and close the air discharge hole (101) such that air in the air residence space (102) is discharged to the outside through the air discharge hole (101);

a needle part (300) installed on a bottom surface of the press-fitting block (200), formed to contain a drug made of a predetermined substance, and configured to be exposed to a bottom of the housing (100) and penetrate a patient's skin due to the press-fitting block (200);

a pressing part (400) inserted into and coupled to the air residence space (102) to be positioned above the press-fitting block (200) and configured to push the air in the air residence space (102) toward the press-fitting block (200) to guide downward movement of the press-fitting block (200); and a protective film (500) formed to be attached to seal the bottom end of the housing (100) and prevent contaminants contained in air from entering the needle part (300).

2. The microneedle of claim 1, wherein a stopper (103) is formed along the inner circumferential surface of the air residence space (102) to prevent a lower end of the pressing part (400) from coming in contact with the press-fitting block (200).

3. The microneedle of claim 1, wherein catching steps (104) are formed on an edge of the bottom end of the housing (100) and configured to allow an edge of the bottom surface of the press-fitting block (200) to be caught such that the catching steps block movement of the press-fitting block (200) toward the bottom end of the housing (100) by a predetermined distance or more; and an adhesive film (105) is disposed on bottom surfaces of the catching steps (104) and configured to be adhered to the patient's skin to prevent movement of the housing (100).

4. The microneedle of claim 1, wherein, in the housing (100), a distance (L) from the air discharge hole (101) to the bottom end of the housing (100) is formed to be relatively larger than a height (H) of the press-fitting block (200).

5. The syringe type-microneedle of claim 1, wherein the drug is configured to:

be coated on an outer surface of the needle part (300);

be dissolved after penetrating the patient's skin; or be accommodated in the needle part (300) and injected after penetrating the patient's skin.

* * * * *